(12) United States Patent
O'Neill (10) Patent No.: US 6,743,017 B2
(45) Date of Patent: Jun. 1, 2004

(54) MANDIBULAR OCCLUSAL INHIBITOR

(75) Inventor: Kathleen A. O'Neill, Newtown Square, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 10/350,920

(22) Filed: Jan. 24, 2003

(65) Prior Publication Data

US 2004/0005529 A1 Jan. 8, 2004

Related U.S. Application Data (60) Provisional application No. 60/393,286, filed on Jul. 2, 2002.

(51) Int. Cl.[7] .................................................. A61C 5/00
(52) U.S. Cl. ........................................ 433/140; 600/238
(58) Field of Search ............................... 433/140, 138, 433/149, 93, 94; 600/238; 128/862, 859, 861, 200.26

(56) References Cited

U.S. PATENT DOCUMENTS

| 4,067,331 | A | * | 1/1978 | Berman | 128/200.26 |
| 5,487,660 | A | * | 1/1996 | Good | 433/3 |
| 5,533,523 | A | * | 7/1996 | Bass et al. | 128/859 |
| 5,590,643 | A | * | 1/1997 | Flam | 128/200.26 |
| 5,894,840 | A | * | 4/1999 | King | 128/200.26 |
| 5,911,576 | A | * | 6/1999 | Ulrich et al. | 433/68 |
| 6,500,002 | B2 | * | 12/2002 | Horiguchi | 433/140 |

* cited by examiner

*Primary Examiner*—Kevin Shaver
*Assistant Examiner*—Melba Bumgarner
(74) *Attorney, Agent, or Firm*—Stephen H. Eland; Dann, Dorfman, Herrell and Skillman (57) ABSTRACT

A device for maintaining a patient's mouth in an open position during a medical procedure is provided. The device includes a cylindrical body configured to be received in the patient's mouth. A flange extending from an edge of the body is configured to engage the face of the patient, and preferably, the device includes a retainer for retaining the body in the patient's mouth.

19 Claims, 6 Drawing Sheets

MANDIBULAR OCCLUSAL INHIBITOR

PRIORITY CLAIM

This application claims priority to U.S. Provisional Patent Application No. 60/393,286, filed Jul. 2, 2002, which is hereby incorporated herein by reference.

FIELD OF THE INVENTION

The present invention relates to a device for holding a patient's mouth in an open position during medical, dental and surgical procedures.

DESCRIPTION OF THE RELATED ART

Medical professionals frequently perform procedures that require the patient's mouth to be held in an open position. For example, a patient's mouth must be held open during endoscopic procedures to provide clearance for an endoscope and other instruments. A patient's mouth must also be held in an open or semi-open position when dental bite-wing x-ray images are taken. A similar need exists in trauma evaluation and diagnosis of spinal injuries.

Spinal injuries require prompt evaluation by emergency health care providers. Early recognition of possible cervical spine injury (CSI) is of critical importance. Spinal injury may be difficult to diagnose in patients who are uncooperative, have altered mental status, or other distracting injuries. In such cases, it is difficult to obtain radiographic imagery to make a proper evaluation of the patient. During the initial assessment, great care must be taken to adequately stabilize the patient's spine and undertake cervical spine radiography for optimal patient evaluation. Obtaining proper cervical spine films, particularly the open-mouth odontoid view (OMV), in the pediatric and adult populations can be a challenging experience even under the best patient circumstances. Patient-related concerns include inability to cooperate during the procedure, repeat films, excessive radiation exposure, and delays in care.

Data from the National Spinal Cord Injury Statistics Center (NSCISC) reports that approximately 10,000 new cases of cervical spine injury (CSI) occur annually, with 1,100 of these cases occurring in children. Boys sustain injury more often than do girls and the most common type of CSI is a combined fracture and dislocation injury. The primary mechanism by which children sustain this serious injury involves blunt trauma from motor vehicle crashes, falls and sports-related accidents. Children with congenital anomalies such as Trisomy 21, Klippel-Feil syndrome, mucopolysaccharidosis are at a greater risk for CSI due to bony abnormalities of the spine and laxity of the neck and spine ligaments.

Although CSI in children is rare, it generally carries a greater degree of morbidity and mortality in the younger pediatric population with associated head trauma. Spinal trauma in the young child often occurs in the higher cervical spine area (C1–C3) due to the child's larger head-to-body ratio and laxity of their ligaments. As the pediatric spine matures, it approaches adult-like configuration by around eight years of age, as described in Herman, M. et al., *Cervical Spine Disorders in Children*, Orthop. Clin. Nor. Amer. 1999, 30(3): 457–465. Although the adult spine can distribute traumatic forces more evenly throughout the cervical vertebrae, they generally have a higher incidence of CSI than children, and sustain primarily lower C-spine injury below the C3 level, as described in Manary, M. et al., *Cervical Spine Injuries in Children*, Ped. Ann. 1996, 25(8): 423–428.

It is estimated that 10–25% of patients with CSI suffer extension of their injuries (paralysis or death) from delays in diagnosis, or unwarranted manipulation in the emergency department (ED) setting. Failure to adequately diagnose CSI promptly can lead to severe neurologic disability and morbidity. Two of the more common errors are failure to obtain adequate C-spine roentgenograms and difficulty in x-ray interpretation.

According to the American College of Radiology Appropriateness Criteria and the American College of Surgeons, the "golden standard" for trauma evaluation of the cervical spine area is the three-view x-ray that includes the lateral, the anteroposterior (AP), and the OMV. See American College of Radiology, *ACR Appropriateness, Criteria for Cervical Spine Trauma*, 1995: 243–246; American College of Surgeons, *Advanced Trauma Life Support (ATLS) Manual*, 1997: 217–229. Proper cervical spine x-rays for the evaluation of neck pain and neck injury in both children and adults are critical. However, obtaining the OMV x-rays can be technically difficult and time consuming for both the patient and the emergency health care provider. See Buhs, C. et al., *The Pediatric Trauma C-spine: Is the Odontoid View Necessary?* J. Ped. Surg. 2000, 35(6): 994–997; Bonadio, W., *Cervical Spine Trauma in Children: Part 1. General Concepts, Normal Anatomy, Radiographic Evaluation*, Am. J. Emerg. Med. 1993, 11(2): 158–165; Schwartz, D. Introduction to Radiology, "*In: Emergency Radiology*", New York: McGraw-Hill, 2000, 1–7, 291; Swischuk, L. et al., *Is the Open-Mouth View Necessary in Children Under 5 Years?*, Ped. Rad. 2000, 30:186–189. Depending on the patient's condition, it may be very difficult to have the patient open their mouth and keep the mouth open while radiography is performed. Problems may be attributed to the patient's age, the patient's mental impairment, unconsciousness, pain or injury that distracts the patient, inability to open the patient's mouth, and difficulties in positioning the patient.

Accordingly, it is desirable to provide a comfortable oral device that may used in a variety of applications, including radiography, to securely hold a patient's mouth in an open position.

SUMMARY OF THE INVENTION

In light of the foregoing, the present invention relates to a device for maintaining a patient's mouth in an open position during a diagnostic, surgical or other medical procedure. The invention may be used in various applications, including but not limited to, radiology, endoscopy, dental treatment and surgical procedures. In radiology, for example, the invention can be used to facilitate OMV x-rays for spinal trauma evaluation. One or more components of the device are formed of radiolucent materials. In this way, the device may be used in applications such as radiography without visually obstructing x-ray images.

One or more inner flanges may be provided on the device that extend into the mouth. The inner flange or flanges may engage the interior of the mouth and teeth to hold the mouth in an open position. Grooved or serrated surfaces may be provided on the inner flanges so that the inner flanges are less prone to sliding or slipping as they contact the patient's teeth. The device may also have one or more outer flanges. In one embodiment of the invention, the outer flange or flanges form loop handles that assist in placing the device in a patient's mouth. In another embodiment of the invention, the outer flange or flanges include rests or tabs that support the patient's lips while the device is inserted in the patient's mouth.

One or more wings may extend from the device to help keep the device in the patient's mouth. In one embodiment of the invention, the wings have solid faces and contain an adhesive pad. The adhesive pad adheres to skin around the patient's mouth when the device is inserted in the patient's mouth to keep the device in place. In another embodiment of the invention, the wings have hollow apertures. Adhesive tape may be wrapped through the apertures and applied to the skin around the patient's mouth to keep the inserted device in place. Alternatively, a flexible strap may be inserted through the apertures and pulled over the patient's head to assist in holding the inserted device in place. The invention will be more fully described by reference to the following drawings.

DETAILED DESCRIPTION OF THE PRESENT INVENTION

Figure 1:
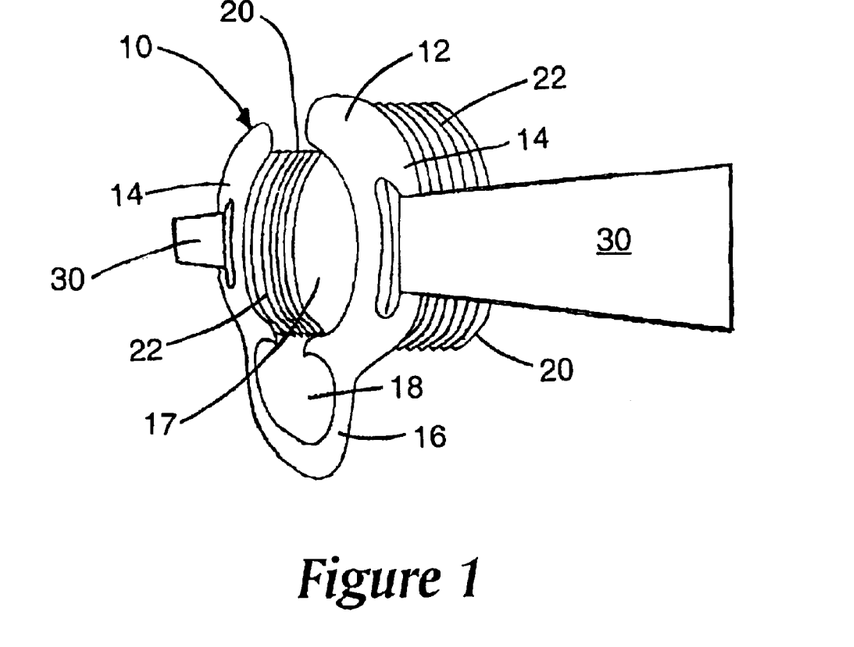
FIG. 1 is a perspective view of a mouth positioning device having ridged inner flanges in accordance with the present invention.

Referring now to FIGS. 1–11 generally, and FIG. 1 in particular, a mouth positioning device in accordance with the present invention is shown and designated generally by reference number 10. Wherever possible, the same reference numbers will be used throughout the drawings and the description to refer to the same or like parts.

FIG. 1 is a perspective view of the mouth positioning device 10. The device 10 is configured to support and maintain a patient's mouth in an open position to permit completion of various medical, dental and surgical procedures. The device 10 may be used in a number of applications, including but not limited to, radiology, endoscopy, dentistry and surgery. In radiology, the device 10 can be used in emergency trauma rooms or in free-standing radiology suites.

Figure 2:
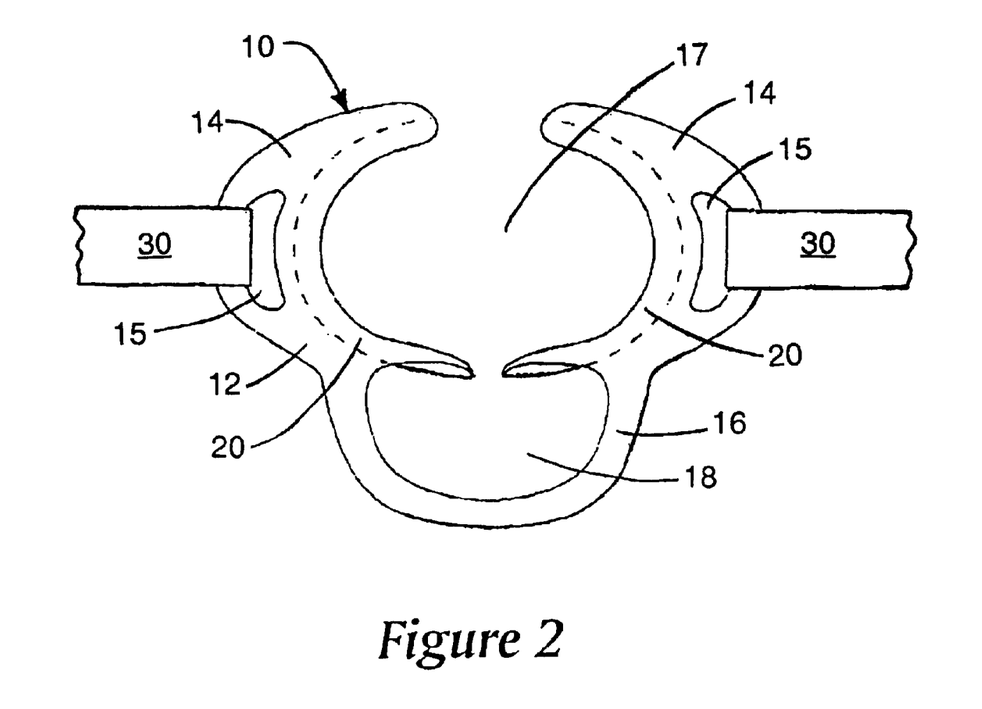
FIG. 2 is a fragmented front elevation view of the device of FIG. 1.

Referring now to FIGS. 1–2, the device 10 comprises a body portion 12. The body portion is formed of one or more radiolucent materials that permit passage of radiation or x-rays. In this way, radiographic images can be obtained with the device in place, with minimal obstruction or visible interference from the device. A variety of radiolucent materials may be used, including but not limited to composites and thermoplastics.

The body portion 12 is formed of a soft, light-weight radiolucent material, such as a soft polymer, composite or thermoplastic. As mentioned above, plastics are radiolucent, which permits them to be used in radiography. Soft plastics also provide sufficient rigidity to support a patient's jaw while offering some flexibility to reduce the stresses that may be exerted on the patient's mouth. Lighter-weight plastic materials also reduce the potential for tooth chipping or damage that could occur when the device 10 is inserted quickly, such as in an emergency procedure. Preferably, the device 10 is formed of an inexpensive and disposable material, such as polyethylene.

In FIG. 1, the body portion 12 comprises a pair of crescent-shaped wings 14 connected by a loop handle 16. The wings 14 form a rounded orifice or passage 17 through which instruments may be inserted during medical procedures. A pair of inner flanges 20 extend from the wings 14 in a direction that is generally normal to the orientation of the wings. The inner flanges 20 face one another in a generally symmetrical and oval-shaped configuration that surrounds the passage 17. As such, the inner flanges 20 are configured to be inserted into the open mouth of a patient. The body portion 12 accommodates the insertion of instruments having various sizes. The passage 17 may provide an opening up to 80 millimeters wide and accommodate a maximum French size greater than 60. Preferably, the passage 17 provides an opening that is at least 60 millimeters wide and accommodates a maximum French size of at least 60.

Figure 3:
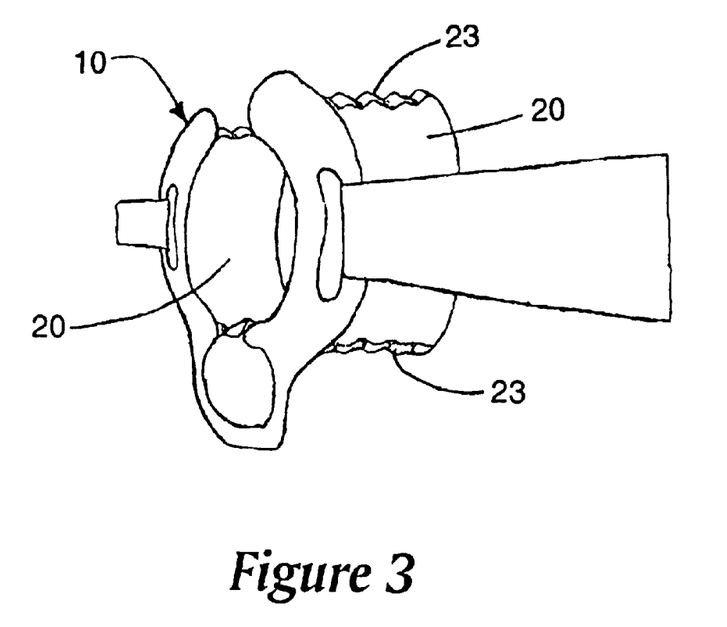
FIG. 3 is a perspective view of an alternate embodiment of the present invention having inner flanges with occlusal recesses.

The inner flanges 20 are configured to contact a patient's teeth in a stable and comfortable position after the device 10 is inserted into the patient's mouth. The device 10 is structured so that the patient's teeth engage or clamp down on the inner flanges 20. Preferably, the inner flanges 20 comprise surfaces that grip the patient's teeth and minimize sliding or shifting of the device 10 in the patient's mouth. Slide resistant surfaces may be formed in a number of ways. For example, the inner flanges 20 may be molded to provide a contoured or textured surface that frictionally engages the patient's teeth. In FIG. 1, the inner flanges 20 are shown with a series of ridges or serrations 22 that provide resistance to sliding against the patient's teeth. Alternatively, the inner flanges 20 may be contoured with occlusal recesses 23 that conform generally to the patient's teeth, as shown in FIG. 3.

Figure 4:
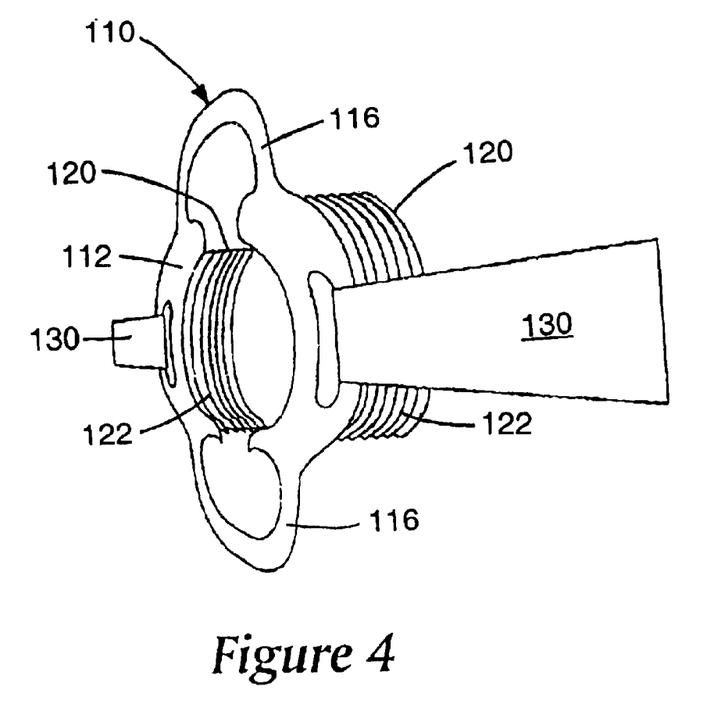
FIG. 4 is a perspective view of an alternate embodiment of the present invention having a pair of loop handles.

Referring again to FIGS. 1–2, the loop handle 16 provides a mechanism for handling the device and guiding the device 10 into a patient's mouth. In this way, the medical professional avoids direct handling of the inner flanges 20 and other components that are inserted into the patient's mouth. The loop handle 16 forms a rounded opening 18 that permits insertion of one or more human fingers. The device 10 may have one loop handle 16, as shown in FIGS. 1–2. However, the present invention may also be provided with more than one loop handle. Referring to FIG. 4, an alternate device 110 is shown. The components of device 110 that are similar to components of the device 10 are identified by the same reference number plus 100. Device 110 has two loop handles 116 that provide a mechanism for handling and guiding the device 110 into a patient's mouth.

For some patients, such as small children, the patient's mouth may be smaller than the outer periphery of the inner flanges 20. Referring again to FIG. 2, the loop handle 16 provides a flexible bridge that can be bent to permit insertion of the device 10 into the patient's mouth. The handle 16 is formed of a thin radiolucent material that flexes to adjust the size of the device as it is inserted into a patient's mouth. More specifically, the handle 16 is formed of a resiliently flexible material, such as plastic, that bends to permit the wings 14 to be compressed or squeezed together. In this way, the wings 14 and inner flanges 20 can be compressed inwardly as necessary so that the inner flanges fit into a patient's mouth opening. When compressive force is released from the wings 14, the resiliency of the loop handle 16 creates a restoring force that restores the handle, wings and inner flanges 20 to their original positions. Preferably, the resiliency of the loop handle provides a relatively weak restoring force that can be overcome by the jaw strength of most patients. In this way, the loop handle 16 provides a snug fit in the patient's mouth without causing the inner flanges to bear harshly against the sides of the patient's mouth.

Referring again to FIG. 1, the device 10 is configured to be inserted into a patient's mouth so that the body portion 12 contacts the facial area around the patient's mouth. The device 10 may be secured in the patient's mouth to prevent the patient from spitting out or removing the device during the performance of medical procedures. This may be desirable in cases where the device is inserted in the mouth of a traumatized or uncooperative patient in need of prompt medical evaluation. Referring to FIG. 2, the wings 14 comprise a pair of apertures 15 that extend through the wings. The apertures 15 may be used with a variety of materials to hold and maintain the device 10 securely in the patient's mouth. By providing the apertures 15, the amount of material required to make the body portion 12 is reduced, resulting in a lighter-weight and lower cost product. In addition, the apertures 15 add flexibility to the device to improve patient comfort.

Figure 9:
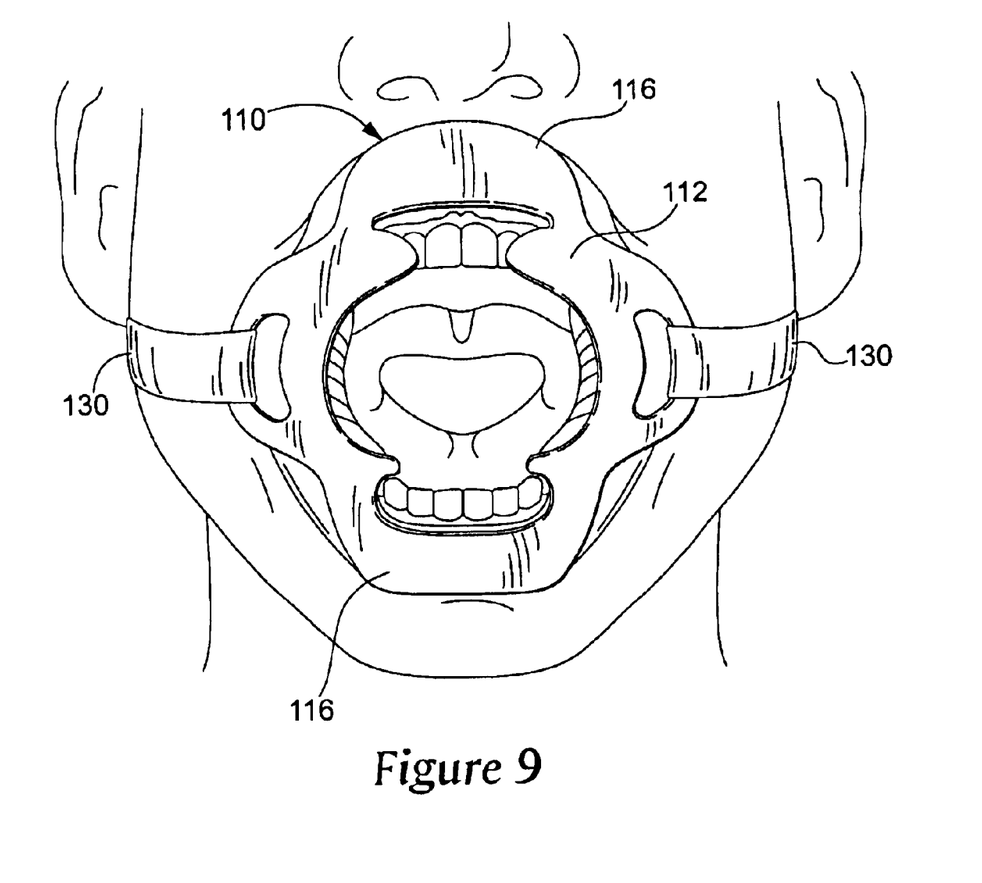
FIG. 9 is a front elevation view of the device of FIG. 4 inserted in the mouth of a patient.

In FIG. 2, the device 10 is shown with strips of adhesive tape 30 inserted through the apertures. The adhesive strips 30 are configured to contact and adhere to skin around the patient's face when the device is inserted into the patient's mouth. In particular, each adhesive strip 30 is inserted through an aperture 15 such that a side with adhesive is oriented toward the patient's face. As such, the device 10 can be inserted into a patient's mouth, and the adhesive tape 30 may applied to the skin around the patient's mouth to hold the device in place. Referring to FIG. 9, the device 110 of FIG. 4 is shown secured to a patient's face with adhesive tape strips 130. The strips may contain any adhesive compound suitable for contact with skin, such as adhesive compounds used on bandages. The adhesive strips are preferably water resistant to provide a bond that withstands moisture, such as patient perspiration or saliva.

Figure 5:
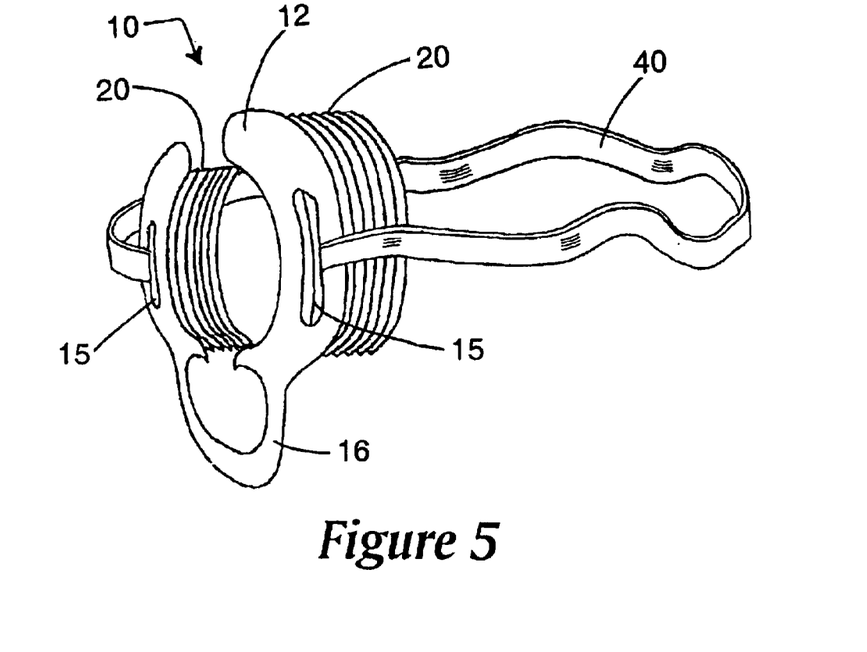
FIG. 5 is a perspective view of the device of FIG. 1 having an elastic strap for securing the device to a patient.

The apertures 15 may also be used with a flexible strap 40 to hold the device 10 in place. Referring to FIG. 5, the device 10 is shown with a large strap 40 having two ends inserted through apertures 15. The strap 40 is preferably an elastic strap that may be pulled around the patient's head prior to inserting the device 10 in the patient's mouth. Preferably, the tension in the strap 40 is sufficient such that the strap tightly engages the patient's head and securely holds the device 10 in the patient's mouth. The strap 40 may be provided either as an alternative to the adhesive strips 30, or in conjunction with the adhesive strips. In addition, the strap 40 may formed of a radiolucent material, such as a thin plastic, for use in radiography.

Figure 6:
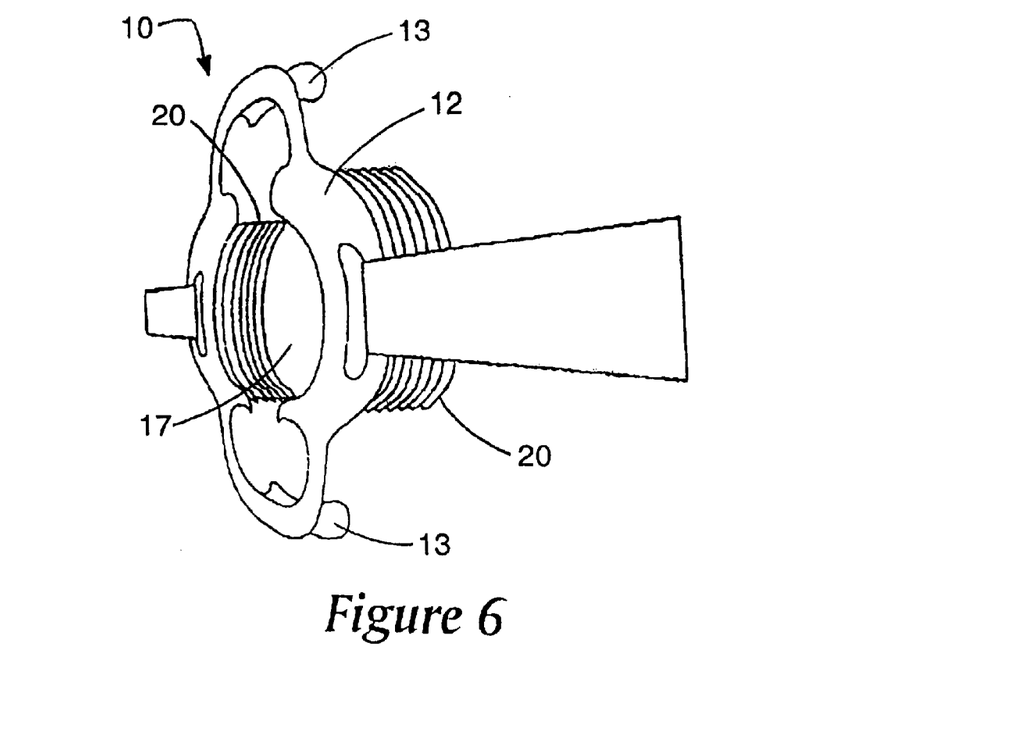
FIG. 6 is a perspective view of an alternate embodiment of the present invention having a pair of rests for supporting the patient's lips while the device is inserted in the patient's mouth.

As stated earlier, the device 10 is configured to be inserted into a patient's mouth so that the body portion 12 contacts the facial area around the patient's mouth. Preferably, the body portion 12 has one or more lip rests 13, as shown in FIG. 6. The lip rests 13 are configured to spread and hold the patient's lips apart while the device 10 is inserted in the patient's mouth. The lip rests 13 curve inwardly toward the central passage 17 and provide a smooth surface that supports the patient's lips in a comfortable position.

In the preferred embodiment, the device 10 may be produced with a flavor element to be tasted by the patient when the device is inserted in the patient's mouth. The flavoring element may be one a variety of compositions or flavors, such as mint or citrus for example. The flavoring is applied to the inner flanges 20, which extend into the patient's mouth when the device is in use. The flavor element may be deposited on the device using a variety of substances or processes. For example, the flavor element may be deposited with a spray, grease or coating applied on the device 10. Moreover, the flavor element may be mixed into the material that forms the device to encapsulate the flavoring element to thereby preserve the flavor element.

Figure 7:
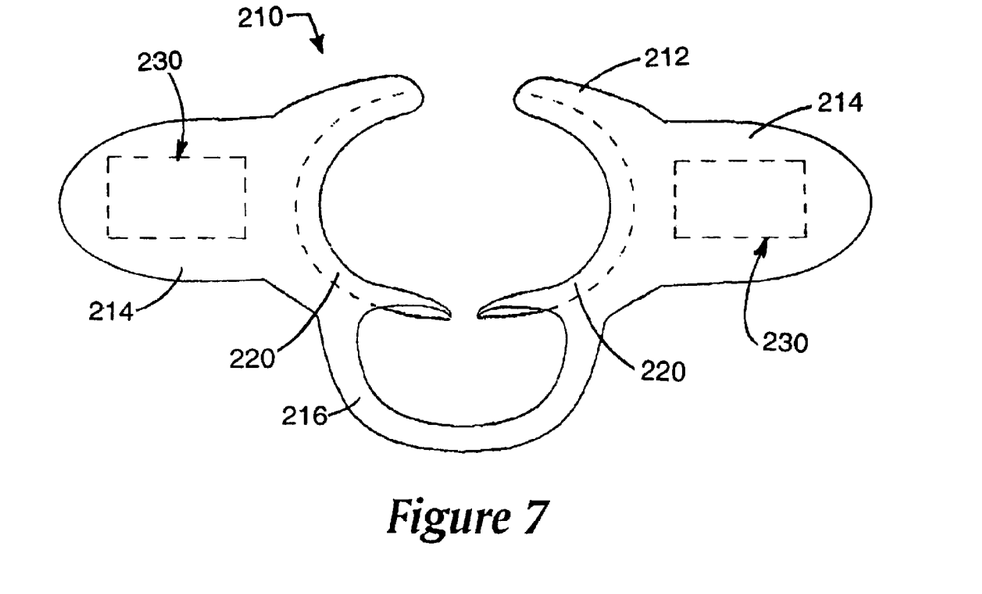
FIG. 7 is a front elevation view of an alternate embodiment of the present invention having adhesive pads for securing the device to a patient.
Figure 8:
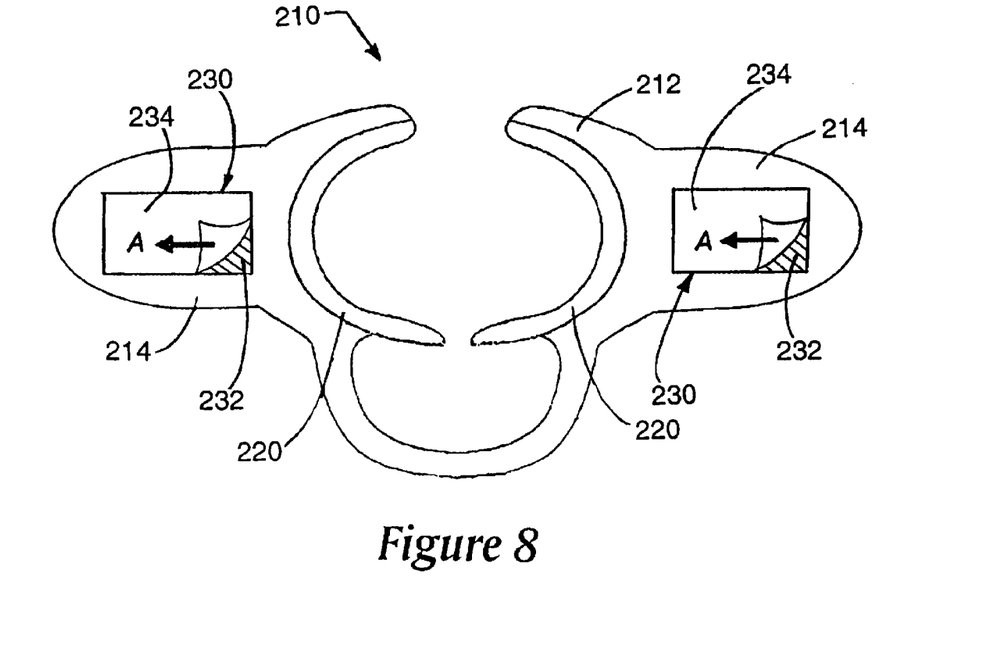
FIG. 8 is a rear elevation view of the device of FIG. 7.

Referring now to FIGS. 7–8, an alternate embodiment in accordance with the present invention is shown and designated generally by reference number 210. Components that are similar to components of the device 10 are identified by the same reference number plus 200. The device 210 comprises a body portion 212 and a pair of solid wings 214 that extend outwardly from the body portion, similar to the previous embodiment. The solid wings 214 each comprise an adhesive pad 230 configured to hold the device in place. In particular, each adhesive pad 230 has a front adhesive face 232 that may be applied to the skin around the patient's mouth to hold the device 210 in place. Each adhesive pad 230 also has a rear face that is attached to a wing 214. The rear faces of the adhesive pads 230 may be attached to the wings 214 by bonding or any suitable connection. The adhesive faces 232 may contain any adhesive compound suitable for contact with skin, such as adhesive compounds used on bandages. The adhesive compound is preferably water resistant to provide a bond that withstands moisture, such as patient perspiration or saliva. The front adhesive faces 232 of the adhesive pads 230 may be protected by covers 234 prior to use, as shown in FIG. 8. The covers 234 are configured to be peeled back from the adhesive pads 230, as illustrated by the partially folded corners and arrows marked "A". The covers 234 may be removed to expose the adhesive face immediately prior to inserting the device 210 in the patient's mouth. In this way, the adhesive compound does not dry or come in contact with other materials prior to being applied to the patient's face.

Figure 10:
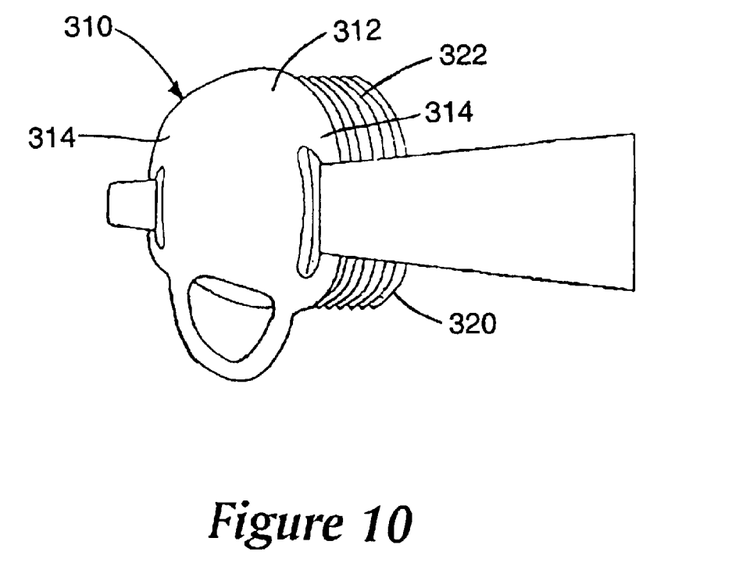
FIG. 10 is a perspective view of an alternate embodiment of the present invention having a solid disk.
Figure 11:
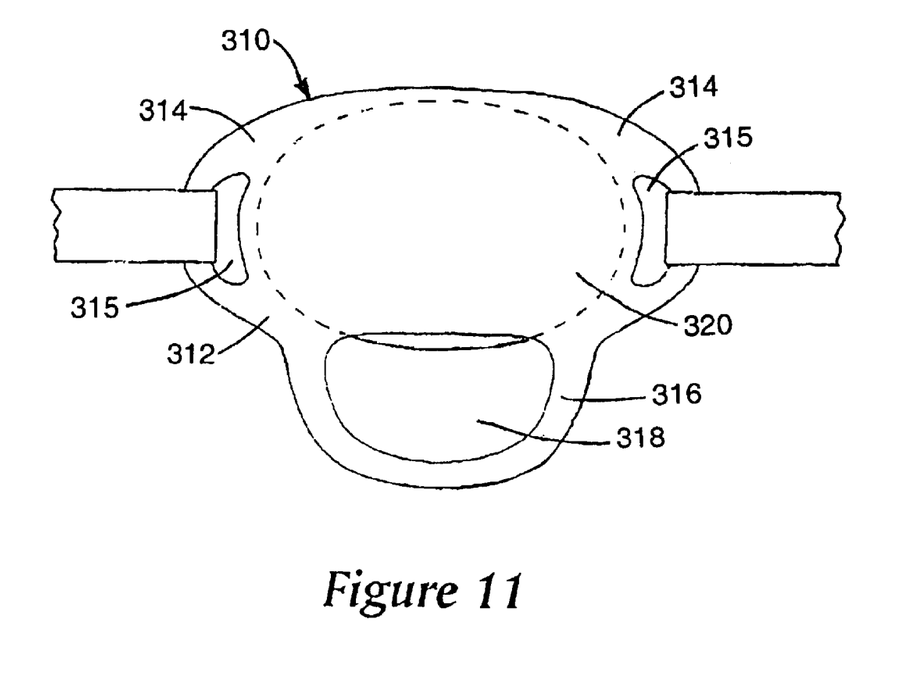
FIG. 11 is a front elevation view of the device of FIG. 10.

Referring now to FIGS. 10–11, another embodiment of the present invention is shown and designated generally by the reference number 310. Components that are similar to components of the device 10 are identified by the same reference number plus 300. The device 310 comprises a body portion 312 formed of a radiolucent material, similar to previous embodiments. Instead of inner flanges, the body portion 312 comprises a solid plate or disk 320 configured to contact a patient's teeth after the device 310 is inserted into the patient's mouth. The disk 320 may be molded to provide a contoured or textured surface that frictionally engages a patient's teeth. In FIG. 10, the disk 320 is shown with a series of ridges or serrations 322 that provide resistance to sliding against a patient's teeth. The disk 320 may be desirable where a more rigid mouth support is required, or where the procedure does not require insertion of equipment through the inserted device 310.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention as set forth in the claims.

What is claimed is:

1. A mouth positioning device, comprising:
   a generally cylindrical bite block configured to be received between a patient's teeth, comprising a first half and a second half and a gap separating the first half from the second half, wherein one end of the bite block terminates in a bottom edge configured to be received within the patient's mouth behind the patient's teeth and a second end of the bite block terminates in a top edge to be positioned in front of the patient's teeth, wherein a thickness of the bite block is the distance between the top and bottom edges of the bite block;
   a bridge connecting the first half and the second half of the bite block, wherein the bridge is flexible to allow the first half to be displaced inwardly toward the second half upon application of an inward force, and wherein the bridge has a thickness that is less than the thickness of the bite block; and
   first and second flanges extending outwardly from the top edge of the bite block and configured to engage the patient's face, wherein an edge of the first flange terminates in a first terminal edge spaced away from the bite block and an edge of the second flange terminates in a second terminal edge spaced away from the bite block
   wherein the distance between the first and second terminal edges is greater than the thickness of the bite block.

2. The device of claim 1 wherein the bite block comprises a plurality of serrations formed on an exterior surface of the bite block.

3. The device of claim 2 wherein the bite block, serrations and first and second flanges are molded as a single part.

4. The device of claim 1 comprising a retainer configured to retain the bite block in the patient's mouth.

5. The device of claim 4 wherein the retainer comprises a pair of adhesive strips spaced apart from one another and connected to a surface of the first and second flanges to releasably engage the patient's face.

6. The device of claim 4 wherein the retainer comprises a loop of flexible material configured to form a strap extending around the patient's head.

7. The device of claim 1 comprising a lip rest configured to engage a lip of the patient.

8. The device of claim 7 comprising a second lip rest configured to engage a lip of the patient, wherein the second lip rest is spaced apart from the first lip rest.

9. The device of claim 8 wherein the first and second lip rests are configured to retain the patient's lips apart while the device is inserted into the patient.

10. The device of claim 7 wherein the lip rest projects away from a surface of the bridge.

11. A mouth positioning device, comprising:
    a bite block configured to be received between a patient's teeth, comprising first and second halves and a gap separating the first half from the second half, wherein the bite block has a thickness;
    a bridge connecting the first half and the second half of the bite block, wherein the bridge is flexible to allow the first half to be displaced inwardly toward the second half upon application of an inward force, and wherein the bridge has a thickness that is less than the thickness of the bite block;
    a first flange extending outwardly from a top edge of the second half of the bite block and configured to engage the patient's face;
    a second flange extending outwardly from a top edge of the first half of the bite block and configured to engage the patient's face; and
    a retainer configured to retain the bite block in the patient's mouth.

12. The device of claim 11 wherein the gap is configured to separate the first half of the bite block from the second half of the bite block so that the two halves do not contact each other when the flexible bridge is in a relaxed state and the bridge is formed of a resiliently flexible material.

13. The device of claim 11 wherein the retainer comprises a pair of adhesive strips spaced apart from one another and connected to a surface of the first and second flanges to releasably engage the patient's face.

14. The device of claim 11 wherein the retainer comprises a loop of flexible material configured to form a strap extending around the patient's head.

15. The device of claim 11 comprising a second bridge spaced apart from the first bridge, connecting the first and second halves of the bite block.

16. The device of claim 11 comprising a lip rest configured to engage a lip of the patient.

17. The device of claim 16 comprising a second lip rest configured to engage a lip of the patient, wherein the second lip rest is spaced apart from the first lip rest.

18. The device of claim 17 wherein the first and second lip rests are configured to retain the patient's lips apart while the device is inserted into the patient.

19. The device of claim 16 wherein the lip rest projects away from a surface of the bridge.

* * * * *